United States Patent [19]

Rall et al.

[11] Patent Number: 4,579,462

[45] Date of Patent: Apr. 1, 1986

[54] DEW POINT MEASURING APPARATUS

[75] Inventors: Dieter Rall, Newport Beach; David R. Hornbaker, La Habra, both of Calif.

[73] Assignee: Trans-Met Engineering, Inc., Anaheim, Calif.

[21] Appl. No.: 735,747

[22] Filed: May 20, 1985

[51] Int. Cl.$^4$ ............................................. G01N 25/68
[52] U.S. Cl. ........................................ 374/28; 374/16; 374/25
[58] Field of Search ..................... 374/16, 25, 27, 28, 374/15, 29, 30; 73/336.5; 364/509

[56] References Cited

U.S. PATENT DOCUMENTS

| | | | |
|---|---|---|---|
| 1,986,529 | 1/1935 | Ray | 374/28 |
| 2,316,624 | 4/1943 | Romanelli | 374/15 |
| 2,415,776 | 2/1947 | Walton | 374/15 |
| 2,588,355 | 3/1952 | Burr et al. | 374/15 |
| 2,680,371 | 6/1954 | Donath | 374/28 |
| 2,904,995 | 9/1959 | Obermaier | 374/28 |
| 3,134,259 | 5/1964 | Hallmarken | 374/28 |
| 3,177,716 | 4/1965 | Warman | 374/18 |
| 3,280,618 | 10/1966 | Ballinger | 374/28 |
| 3,283,561 | 11/1966 | Fricke | 374/15 |
| 3,293,901 | 12/1966 | Van Scoyoc et al. | 374/21 |
| 3,396,574 | 8/1968 | Hanlein | 374/28 |
| 3,491,583 | 1/1970 | Roussel et al. | 374/28 |
| 3,589,169 | 6/1971 | Lafitte et al. | 374/28 |
| 4,028,942 | 6/1977 | Gardiner | 73/335 |
| 4,276,768 | 7/1981 | Dadachanji | 374/28 |
| 4,408,568 | 10/1983 | Wynnyckyj et al. | 374/27 |

FOREIGN PATENT DOCUMENTS

| | | | |
|---|---|---|---|
| 0508728 | 3/1976 | U.S.S.R. | 374/15 |
| 0928206 | 5/1982 | U.S.S.R. | 374/16 |
| 1084625 | 4/1984 | U.S.S.R. | 374/27 |

Primary Examiner—Charles Frankfort
Assistant Examiner—Thomas B. Will
Attorney, Agent, or Firm—Fulwider, Patton, Rieber, Lee & Utecht

[57] ABSTRACT

Apparatus for determining the relative humidity of an atmosphere by measuring the dew point of the atmosphere. The dew point is measured by lowering the temperature of a condensing or sensing surface associated with a heat flow sensor. When condensation begins to occur this is detected by the heat flow sensor as a change in the rate of heat flow through the condensing surface. In one embodiment a pair of heat flow sensors are employed, one maintained at a slightly lower temperature than the other. The sensors are connected in series opposition so that output signals due to background or convective heat transfer are cancelled, any change in the combined output signal of the two sensors then indicating heat flow resulting from condensation. The temperature of the cooler face will be the dew point temperature. Two arrangements of sensors are disclosed.

14 Claims, 6 Drawing Figures

DEW POINT MEASURING APPARATUS

BACKGROUND OF THE INVENTION

1. Field of the Invention

The present invention relates generally to apparatus for measuring the dew point temperature of a gaseous atmosphere for establishing its relative humidity, and in particular to apparatus for measuring the dew point temperature of hot, dirty air of the kind commonly found in industrial environments such as drying systems.

2. Prior Art

Industrial process drying is typically accomplished by circulating hot, dry air over or through a wet product. When the air becomes saturated with moisture, it must be replaced with fresh air. Large quantities of energy are used in heating this replacement air, much of which energy will be wasted if a given quantity of air is replaced before its full drying capacity has been used. On the other hand, the drying process will become inefficient if the air is allowed to remain in the system after it has become saturated with moisture. To achieve optimum efficiency, therefore, it is necessary to use a system controller that can cause the air in the dryer to be replaced at the proper time, and this controller must in turn be provided with a sensor to measure the relative humidity of the air in the dryer. In this regard, "humidity" is the amount of water vapor present in a given quantity of air. If the amount of water vapor present is less than the maximum possible at a given temperature, the amount is expressed in terms of relative humidity. "Relative humidity" is the actual mass of moisture in a given quantity of air divided by the mass of moisture that the same volume and temperature of air would contain if it were completely saturated.

The "dew point" is the temperature at which air with a given moisture content becomes saturated. This measurement is accomplished by artificially lowering the temperature of a surface and then noting the temperature at which moisture first condenses. Dew point temperatures can be converted directly to relative humidity measurements by reference to appropriate charts or tables. Although the foregoing discussion relates to water and air, it is equally applicable to the condensation of other liquids from other gases.

A dew point sensor for use in industrial environments should be able to operate with an accuracy of 5% or better in an atmosphere having a temperature between 200 and 300 degrees Fahrenheit and a relative humidity between 50% and 100% The sensor must be unaffected by the contaminants that are often present in industrial drying operations.

Many types of dew point sensors are known to the art. They indicate the relative humidity of an atmosphere indirectly by directly measuring the dew point temperature, as previously discussed.

Some dew point sensors are capacitive and resistive devices and employ a moisture-sensitive material to sense condensation. The moisture-sensitive material is formed into a condensation surface on the dew point sensor, and heat is slowly removed from the sensor until condensation begins. The moisture-sensitive material reacts to the presence of the moisture of condensation, for example by changing resistance. The temperature of the sensor is continuously monitored, and when this change of resistance is detected the temperature is recorded. From this temperature, the relative humidity can be determined by reference to the tables mentioned.

Another prior art form of dew point sensor is a condensing mirror type provided with a reflective surface. When the temperature of the reflective surface is reduced to the dew point temperature, condensation takes place The moisture of condensation is detected either by visual inspection or by the use of a photocell or other light-sensitive device that responds to the change in reflectivity caused by the presence of moisture Unfortunately, none of the dew point measuring instruments just described is able adequately to satisfy the requirements for use in industrial processes. The high temperatures that occur in industrial processes damage the components used in many sensors, and the contaminants often found in such processes alter the absorption properties of many moisture-sensitive sensors and cloud the reflecting surfaces of reflector type sensors.

Various other methods of achieving acceptable accuracy under the conditions of industrial processes have been attempted. One such device is disclosed in U.S. Pat. No. 2,680,371 issued to Donath on June 8, 1954. The Donath apparatus takes advantage of the fact that water gives up heat when it changes from its gaseous to its liquid state. This effect is the converse of the well-known cooling effect experienced when water evaporates. Just as water chills the surface from which it evaporates, so it warms the surface upon which it condenses. The heat given off by condensing water is called the "heat of condensation", and the presence of this heat is indirectly detected by the Donath apparatus.

The Donath device is comprised of a reflecting condensation element; means to measure the temperature of the element; means to slowly reduce the temperature of the element by applying a coolant to its back side; and means to expose the front side of the element to the gaseous mixture to be tested. As the element cools past the dew point of the mixture of gases under test, condensation takes place. The temperature of the element rises slightly as the element absorbs the heat of condensation, and this rise in temperature is used to indicate the occurrence of condensation The principal drawback to the Donath apparatus is that it does not actually detect the heat of condensation. Rather, it measures the temperature of the sensing element. Although the heat of condensation will cause the temperature of the sensing element to rise, there is a finite time delay between the occurrence of condensation and the diffusion of the heat of condensation throughout the element. Since the temperature of the element rises only in response to the latter event, the accuracy of the Donath apparatus is inherently limited.

The apparatus disclosed in U.S. Pat. No. 2,904,95, issued to Obermaier on Dec. 10, 1953, seeks to overcome the drawbacks of the Donath apparatus by providing a split sensing element. One part of the element is insulated from moisture such that its temperature is unaffected by the occurrence of condensation, and the difference in temperature between the insulated and the uninsulated parts is then compared. Although this arrangement is an improvement over the Donath apparatus, it still suffers from the inherent limitation that what is actually measured is the change in the temperature of the element rather than the heat of condensation.

U.S. Pat. No. 3,396,574, issued to Hanlein, et al., on July 9, 1965, also discloses apparatus for measuring the increase in temperature of a sensing element that results from the heat of condensation. The Hanlein apparatus employs a Peltier device to accomplish slow cooling of the sensing element, and it uses two thermocouples to detect the increase in the temperature of the sensing element that occurs after the heat of condensation has diffused through the sensing element. Like the Donath and Obermaier inventions, the Hanlein invention uses the event of the increase in temperature of the sensing element to approximate the event of the transfer of the heat of condensation to the element. The Hanlein device is therefore subject to the same limitations of accuracy.

It will be apparent from the foregoing that there is a need for a dew point measuring apparatus that can function in the hostile environment commonly present in industrial systems and that is not subject to the errors inherent in sensing devices known to the art. The present invention satisfies this need.

SUMMARY OF THE INVENTION

The dew point measuring apparatus of the present invention is characterized by a heat flow sensor which, in one embodiment, comprises a condensation surface and an embedded differential thermopile. The heat flow sensor measures the flow of heat into the surface rather than the temperature of the surface. It senses the exothermic release or endothermic absorption of heat as moisture condenses on or evaporates from the surface at the dew point temperature. When the apparatus is used to determine the relative humidity of a gaseous atmosphere, the temperature of the sensor is slowly lowered until the dew point of the atmosphere is reached. As soon as condensation begins, heat of condensation is released from the condensate and flows into the condensation surface. The heat flow sensor responds virtually instantaneously to this heat flow, thereby permitting a much more precise determination of the atmosphere's dew point, and hence of its relative humidity, than can be obtained by sensors known to the art.

In one practical application the apparatus of the invention includes a pair of heat flow sensors mounted adjacent a heat sink. A coolant is circulated through the heat sink to slowly reduce the temperature of the sensors. A heater is provided which is actuable to raise the temperature of the sensors. By actuating and deactuating the heater the temperature of the sensors can be cycled up and down through the dew point of a gas or atmosphere under test, thereby permitting the atmosphere's dew point to be tracked or followed, and measured as often as desired. One of the sensors is kept at a slightly higher temperature than the other, and the output signals from the two sensors are compared, as by connection in series opposition. A stream of gas under test is passed over the sensors. A relatively sudden change or imbalance in the signal from the oppositely electrically connected sensors occurs as moisture condenses on the cooler sensor and the exothermic heat of condensation is released. The surface temperature of the cooler sensor at that instant is the dew point of the gas. This can be used to determine from an appropriate table the relative humidity of the atmosphere.

The use of two heat flow sensors rather than only one has been found to give much better noise immunity. A first sensor is thermally directly associated with the heat sink so that its temperature falls relatively fast in response to the coolant circulating through the heat sink. The second sensor is also thermally associated with the heat sink, but through a path providing a higher thermal resistance. Consequently, its temperature always lags that of the first sensor in response to the coolant.

Since the first sensor is at all times slightly cooler than the second sensor, when the sensors are cooled condensation occurs first on the first sensor because the first sensor reaches the dew point temperature before the second sensor. When such condensation occurs on the first sensor, the heat of condensation is released. This heat flows through the surface and, by continuity of thermal conduction, through the first sensor and into the heat sink, causing an immediate change in the signal from the first heat flow sensor. However, since the second sensor is slightly warmer there is no condensation on it and it generates no change in signal due to condensation. The resulting overall change in output signal from the two heat flow sensors indicates condensation has occurred.

A temperature sensing element is located in the surface of the first sensor and its temperature at the instant of output signal change constitutes the dew point temperature.

The differential thermopile employed in the embodiment mentioned is made up of a number of individual thermocouple junctions connected in series with the differential junctions placed on opposite sides of a very thin thermal barrier. As heat flows across the barrier the thermopile generates an electrical signal proportional to the rate of heat flowing through it. It should be understood that other forms of heat flow sensors could be used instead, if desired.

The present measuring apparatus is adapted for use in association with an industrial process dryer for automatic control of the humidity of the drying atmosphere. A typical dryer comprises a source of heat for heating the atmosphere; a blower for bringing fresh, dry air into the dryer; a controllable air outlet for letting saturated air out; and sensors to monitor the temperature and pressure of the atmosphere. In operation, the air outlet is initially closed to permit the atmosphere inside the dryer to be warmed by the heat source. Articles in the dryer begin to dry and the relative humidity of the atmosphere rises. A sample of the atmosphere is brought past a pair of heat flow sensors, which are cooled to effect condensation and establish the dew point. The detected dew point is compared with a desired or programmed dew point that is automatically computed from the predetermined desired relative humidity and the measured temperature and pressure of the drying atmosphere. When the measured dew point reaches the desired dew point, a signal is generated to actuate the blower and the air outlet to expel moist air and admit new, dry air. After each measurement of relative humidity, a heat source associated with the sensors is actuated for a time sufficient to the heat sensors to a temperature above the dew point. The cycle is repeated upon deactuation of the heater and subsequent cooling of the sensors.

The present invention represents a significant advance in apparatus for determining the relative humidity of an atmosphere. Heretofore, as previously indicated, dew point measurement apparatus depended on detection of a change in temperature of a sensor in response to condensation. The present apparatus utilizes heat flow sensor means to detect the change in the rate of heat flow which occurs on condensation, giving an immediate indication of such condensation, well in advance of the time it would take for a temperature sensor of the prior art to fully react to such heat flow.

Other aspects and advantages of the present invention will become apparent from the following more detailed description taken in conjunction with the accompanying drawings.

DESCRIPTION OF THE PREFERRED EMBODIMENTS

The present apparatus provides a means for determining the relative humidity of a gas or atmosphere by measuring the dew point of the atmosphere. This is not accomplished by detection of a change in temperature of a sensing element when condensation occurs on the sensing element, but by direct detection of the release of the heat of condensation at the dew point. This affords an immediate, more accurate determination of relative humidity, compared to prior art temperature sensing devices. Such temperature sensing devices are inherently less accurate because of the delay between the heat release and the resulting change in temperature of the temperature sensing element.

The invention has particular application in industrial process drying, which involves heating air, circulating it over or through the wet product, and exhausting it when it is water-laden. The hot exhaust air must be replaced by heated fresh air, thus representing an appreciable energy loss. Consequently, it is important that air not be exhausted until its full drying capacity has been employed. Conversely, if air is maintained in the system too long it becomes excessively wet, and inefficient drying occurs. Reduced energy consumption and process efficiency is obtained when the moisture content of the air is precisely and continuously monitored and controlled.

As previously indicated, the broadly unique aspect of the present invention is the use of a heat flow sensor which indicates the rate of heat flow into a surface of the sensor so that it immediately detects the change in rate of heat flow which occurs when condensation takes place upon such surface. Simultaneous measurement of the temperature of the sensor surface at that precise moment enables determination of the dew point.

As will be seen, although a single heat flow sensor can be employed, it is preferable to use a pair of heat flow sensors. This is for the reason that if the sensing surface temperature is allowed to decrease only a fraction of a degree below dew-point, the heat flow due solely to condensation is low relative to the heat flow which is normally present both during and in the absence of condensation. By employing two matched heat flow sensors in adjacent, side-by-side relation, and maintaining them at slightly different temperatures, condensation takes place on the cooler heat flow sensor. Connecting the sensors in series opposition results in a signal due solely to condensation.

One embodiment of the invention provides a continuous dew point temperature reading. This is done by using the condensation signal from the heat flow sensor means to trigger a heating and cooling cycle operative to cause the temperature of the heat flow sensors to oscillate about the condensation or dew-point temperature. A digital logic circuit reads, stores and up-dates the sensor signals to give the desired continuous record of dew point.

Figure 1:
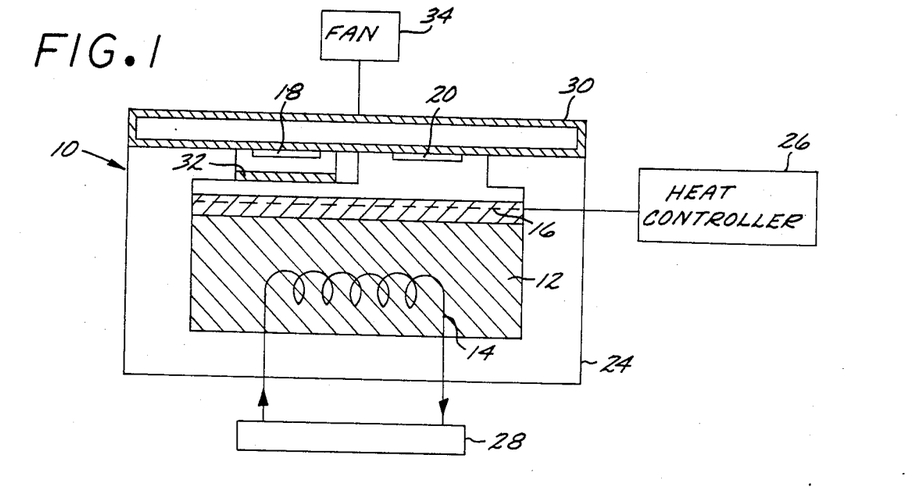
FIG. 1 is a schematic showing of dew point measuring apparatus according to the invention.
Figure 2:
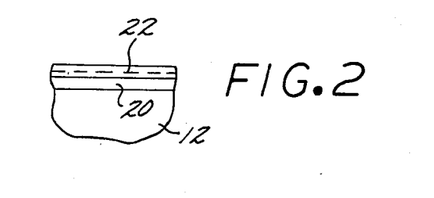
FIG. 2 is an enlarged detail view of the cooler one of the pair of heat flow sensors.

Referring now to the drawings, and particularly to FIGS. 1 and 2, a dew point measuring apparatus 10 is illustrated which comprises, generally, a thermally conductive reference body or heat sink 12; temperature change means for altering the temperature of the heat sink 12, including cooling coils 14 and an electrical resistance heating element embedded in a portion of the heat sink 12 and constituting a heater 16; a pair of matched heat flow sensors 18 and 20; and a temperature sensor 22.

The thermally conductive material of which the heat sink 12 is made can be aluminum, copper or the like and is configured to fit within any suitable external housing 24.

The heater 16 may be a resistance or any other suitable heater for raising the temperature of the mass of the heat sink 12, the leads for the heater 16 being carried through a wall of the housing 24 for connection to a heat controller 26.

The cooling coils 14 are suitably arranged within the heat sink 12 so that circulation of cooling fluid through the coils 14 by means of a coolant controller 28 is operative to drop the temperature of the heat sink 12.

The particular form of heat flow sensor 18 or 20 is not critical to the present invention so long as it is capable of sensing the heat flow through the condensing, sensing or operative faces of the sensors. It could be, for example, a thermopile or an asymptotic type or the like. As will be seen, condensation normally occurs upon the sensing surface of only one of the heat flow sensors, but for convenience both sensing surfaces are sometimes termed condensing surfaces.

The preferred form of heat sensor is a thermoelectric device or very thin differential thermopile. Several hundred thermopile junctions are arranged on either side of a thin thermal barrier and measure the very small temperature gradient which develops across the barrier when heat flows through the heat sensor operative face or condensing surface.

The sensor provides a self-generated signal which is bidirectional, that is, heat flow from the gas into the condensing surface generates a positive signal while heat flow from the condensing surface to the gas generates a negative signal.

The thermopile used is well known in the art and for that reason will not be described in detail, although it is important to note that, like other suitable heat flow sensors, it is adapted to generate a voltage directly proportional to the rate of heat flow through it. Although not shown in detail, each of the heat flow sensors 18 and 20 is approximately one-half inch wide and one inch long, and is potted or embedded in an epoxy resin or the like in a recess in the upper side of the heat sink 12 flush with the inner surface of the lower wall of a laterally elongated air duct or conduit 30.

Suitable insulation coatings are provided to electrically insulate the flow sensors from the adjacent heat sink. With the described arrangement, the flush or operative faces of the sensors are exposed to any heat flow resulting from condensation of moisture in the air flowing through the interior of the duct 30. In the showing of FIG. 1 the air is being forced through the conduit 30 out of the plane of the paper and toward the viewer. Under steady state conditions the effect upon both sensors is the same. Of course, the dimensions and configuration of the duct 30 are arranged to establish laminar or steady state flow conditions across the faces of the sensors 18 and 20, as will be obvious to those skilled in the art.

The absolute velocity of air flow across the sensors is not critical, it being primarily important that there be the same steady state flow past both of them.

Alternate operation of the cooling coils 14 and heater 16 is adapted to cycle the temperature of the heat sink 12 above and below the dew point temperature, as will be seen.

The portions of the heat sink 12 with which the heat sensors 18 and 20 are associated constitute isothermal bodies maintained as close as possible to the same temperature, except for a slight temperature differential provided by a higher thermal resistence material or layer 32 disposed in the thermal path between the heat sensor 18 and the heat sink 12. Although any suitable means could be employed to establish a temperature differential between sensors 18 and 20, the means used is attachment of the underside of sensor 20 directly to the top of the upper surface of the right portion of the heat sink 12. However, the attachment of the underside of the sensor 18 is to an upper left portion or block of the heat sink 12. For convenience, this upper left portion is simply cut away from the parent heat sink 12 and then replaced with the intervening layer 32 providing a thermal barrier in the heat sink 12 at its upper left portion. The layer 32 could simply be a sufficiently thick layer of epoxy adhesive to hold the heat sink portions together and to provide the desired thermal resistance or barrier.

As the heat sink 12 is cooled, heat flows out of the isothermal heat sinks or bodies associated with the sensors 18 and 20, but the higher thermal resistant layer 32 between the sensor 18 and the heat sink 12 causes heat to flow along this path more slowly than the path from the sensor 20 to the heat sink 12. As a result, the temperature of the sensor 18 is always slightly higher than the temperature of the sensor 20 during this cooling phase.

The temperature sensor 22 is embedded in the operative or condensation surface of the heat sensor 20, as best seen in FIG. 2. The temperature sensor 22 may be a conventional thermocouple whose junction is located relatively close to the condensation surface of the heat sensor 20, but preferably it is a resistance type of temperature sensor. In any case, the temperature sensor 22 is operative to generate a voltage proportional to the temperature of the condensation surface of the heat sensor 20.

Assuming a sample of moisture laden air is being driven or drawn through the air conduit 30 by a fan 34 or the like, the condensation surface of the heat sensor 20 eventually reaches the dew point of the air and condensation begins. The heat of condensation released by the moisture as it condenses flows into the condensation surface and through the sensor 20. This heat flow results in an electrical output signal. However, the heat sensor 18 does not detect any change in heat flow due to condensation because its condensation or sensor surface is slightly warmer than that of the sensor 20 and there is no condensation on it. The resulting change in the composite output signal from the sensors 18 and 20 is an immediate indicator that condensation has begun on the condensing surface of the sensor 20. The temperature of the heat sensor 20 condensing surface measured by the temperature sensor 22 at this time is the dew point temperature of the air.

Although the use of two heat flow sensors is preferred, it is possible to use a single sensor in combination with suitable means for enhancing that portion of its output signal due to condensation.

Figure 3:
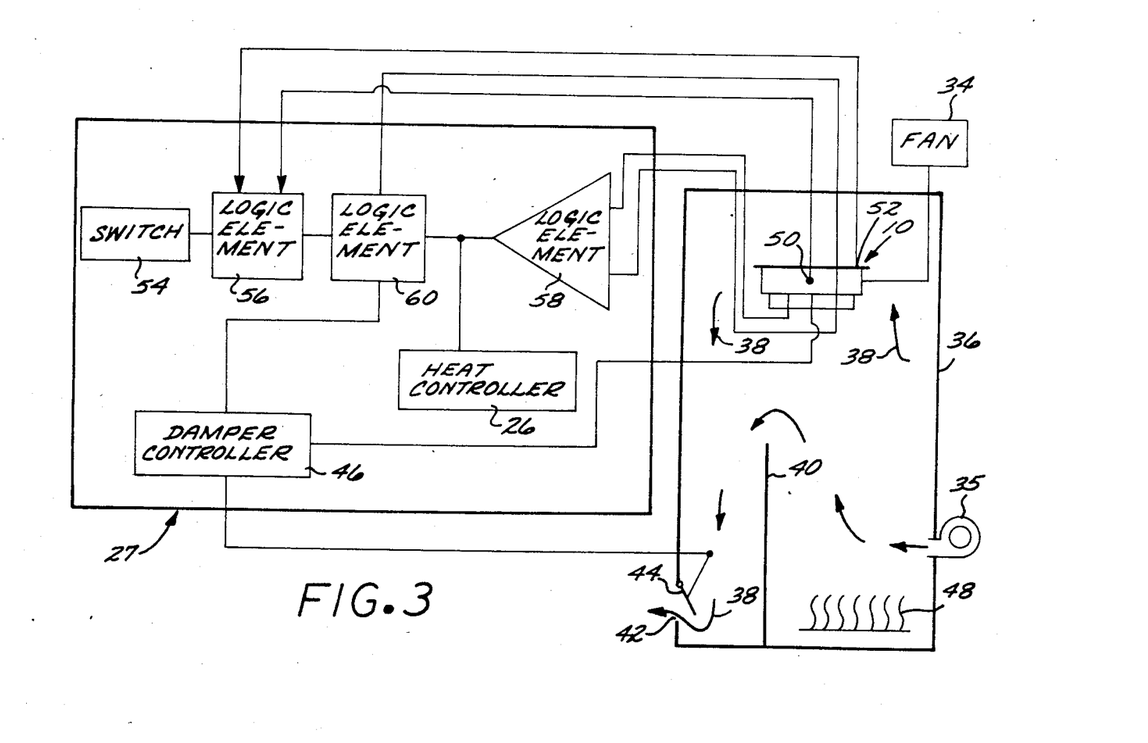
FIG. 3 is a schematic showing of an automatic humidity control system incorporating the present dew point detection apparatus.

The dew point temperature can be utilized to establish the relative humidity of the air by comparison with pre-programmed reference data. More particularly, FIG. 3 illustrates the present dew point measuring apparatus 10 incorporated in an industrial process dryer to enable precise and automatic control of the dryer's relative humidity.

Air is forced into a dryer enclosure 36 by a suitable blower 35, the air flow paths being generally indicated by the arrows 38. The air passes about the dew point measuring apparatus 10, around a baffle 40, and exhausts through an outlet 42 whose size is controlled by a damper 44. The location of the damper 44 is controlled through suitable linkages by a damper controller 46.

A portion or sample of the air within the enclosure 36 is drawn through the dew point measuring apparatus conduit 30 by the fan 34, as previously described. The air in the enclosure 36 is warmed by a burner 48, and its temperature and pressure are measured by temperature and pressure sensors 50 and 52, respectively, which form part of a detecting and control means 27. The desired relative humidity can be set by operation of a set point switch 54. The output of the temperature and pressure sensors 50 and 52 are applied to a logic element 56 which is operative to determine the dew point temperature which corresponds to the desired relative humidity set in at the switch 54 for the temperature and pressure indicated by the sensors 50 and 52. The output signals of the heat flow sensors 18 and 20 are applied to a differential logic element 58.

As with the embodiment of FIG. 1, condensation first occurs on the cooler sensor 20. When this happens, there is a large step change in the composite output signal from the series opposition connected heat flow sensors 18 and 20. This is detected by the logic element 58 which develops an output signal applied to a logic element 60 to signal that condensation has occurred. In response, logic element 60 compares the temperature of the condensation surface of sensor 20 with the desired dew point temperature reported by the logic element 56 and, if the desired dew point has been reached, logic element 60 causes the damper operator or actuator 46 to open the exhaust or air outlet 42 to allow saturated air to move out of the enclosure 36.

The output signal from logic element 58 is also employed to actuate the sensor heat controller 26 and provide heat sufficient to warm the sensors 18 and 20 to a temperature higher than the dew point of the atmosphere, as indicated by a change in the output signal from the sensors. The heat controller 26 then turns off the heater 16, and the coolant passing through the coils 14 gradually cools the sensors 18 and 20 until condensation again is detected, and the cycle repeats.

During successive cycles, if the measured dew point is below the desired dew point, the air outlet 42 remains closed and, as the measured dew point reaches the desired dew point, the air outlet 42 is opened. In this way the relative humidity of the atmosphere within the dryer is accurately and automatically controlled.

Figure 4:
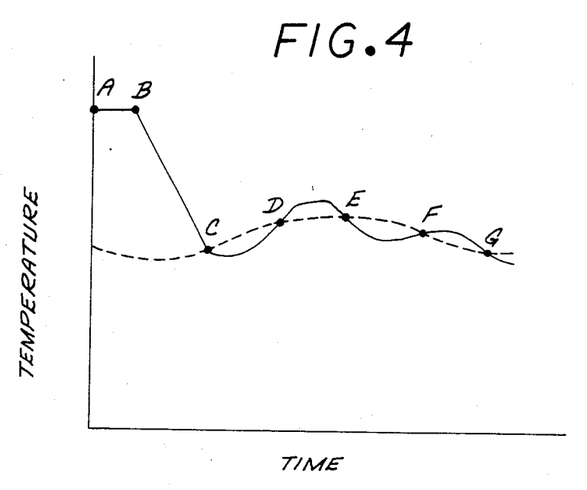
FIG. 4 is a graph showing the heating and cooling cycles of the heat flow sensors.
Figure 5:
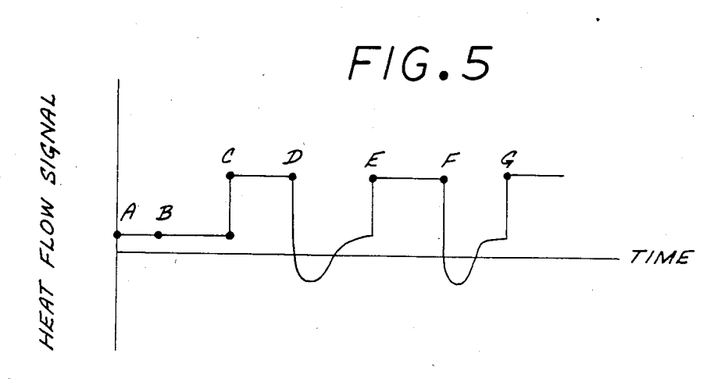
FIG. 5 is a graph showing the changes in heat flow signal corresponding to the heating and cooling cycles of FIG. 4.

This use of the condensation signal to trigger a heating cycle for the heat flow sensors 18 and 20, together with use of the sensors output signal when the condensation is evaporated to start a cooling cycle, causes the temperature of the sensors 18 and 20 to oscillate above and below the condensation or dew point temperature, as seen in FIGS. 4 and 5. Points A to B denote the sensors at equilibrium with the air stream; points B to C indicate cooling of the sensor to the dew point temperature, and the onset of condensation.

The showing in FIG. 5 illustrates the on-off character and direction of the heat flow signal over a period of time, with points A–G corresponding to points A–G of FIG. 4. Thus, in FIG. 5 point C shows the increased heat flow sensor signal at the onset of condensation.

Points C to D indicate the sensor 20 temperature and the output signal when the heater 16 is on and the sensors are rising in temperature, point D indicates when the condensation has been evaporated and the heater 16 is turned off and cooling of the sensors begins; point E denotes attainment of the dew point, occurrence of condensation and the corresponding rise in the heat flow sensor output signal; and points E–G show further cycle repetitions.

Figure 6:
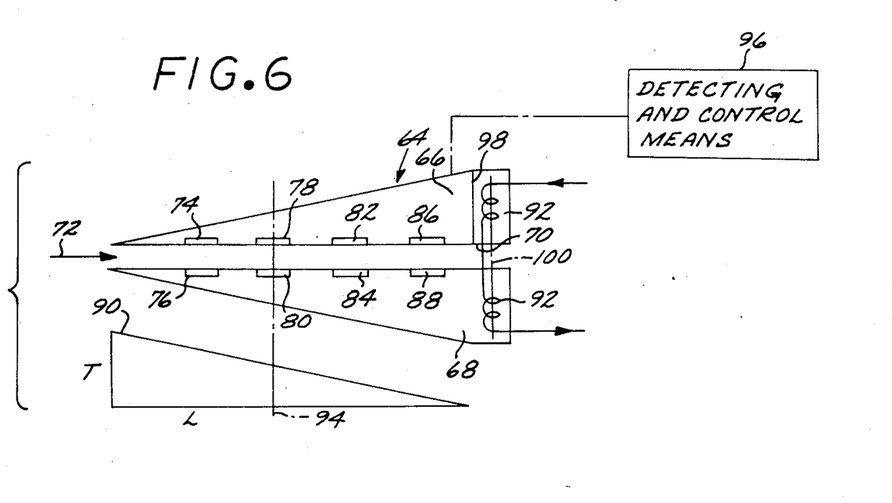
FIG. 6 is a schematic showing of a second embodiment of the present dew point measuring apparatus.

Referring now to FIG. 6, an embodiment of the present dew point measuring apparatus is disclosed which does not require heating and cooling cycles in order to follow or track a changing dew point temperature. The apparatus 64 of FIG. 6 comprises a pair of wedge shaped heat sinks 66 and 68 arranged in spaced relation to define a flow passage 70 between them. The flow passage is properly dimensioned and configured to achieve laminar or steady state flow of the air or other gas flowing through the passage 70 in the direction of the arrow 72.

Pairs of heat sensors identical to the heat sensors 18 and 20 of the first embodiment are arranged in opposed relation in the heat sinks 66 and 68 in flush relation with the surfaces thereof which define the flow passage 70. The pairs of heat sensors are arranged in spaced relation between the upstream and downstream extremities of the passage 70. Thus a pair of sensors 74 and 76 are arranged adjacent the upstream extremity of the passage 70, and next in succession are sensors 78 and 80, sensors 82 and 84, and sensors 86 and 88.

The smaller mass of the upstream or thinner portions of the wedge shaped heat sinks 66 and 68 causes the sensors 74 and 76, for example, to be hotter than the sensors 86 and 88 during steady state conditions, the temperature gradient along the flow passage 70 being indicated at 90 in the showing in the lower portion of the illustration in FIG. 6.

Cooling coils 92 similar to the cooling coils of the first embodiment are arranged in thermal association with the heat sink 66 and 68. In addition, a thermal barrier 98, like the barrier 32, is disposed between the heat sink 66 and the path of thermal association with the cooling coils 92 whereby the heat sink 68 and the sensors 76, 80, 84 and 88 are always slightly cooler than the heat sink 66 and the associated sensors 74, 78, 82 and 86. The phantom line 100 extending between the downstream extremities of the sinks 66 and 68 is to indicate that the sinks 66 and 68 are isothermal except for the presence of the barrier 98, as will be apparent.

Assuming condensation occurs on heat sensor 80, the temperature sensor (not shown) associated with it will indicate the dew point temperature, as schematically indicated by the line 94 and its intersection with the temperature gradiant 90. If the dew point temperature drops, the first condensation will occur downstream from the sensor 80, such as upon the sensor 84. The temperature of the condensation surface of the sensor 84 will then be the new or updated dew point temperature. Thus, cycling of the temperature of the sensors through the dew point temperature line, as schematically illustrated in FIG. 4 for the embodiment of FIG. 3, is not necessary to track or follow a changing dew point temperature.

Although not shown, it will be apparent to those skilled in the art that a fan or the like (not shown) will be necessary to draw sample air through the passage 70, and that suitable detecting and control means 96, similar to the means 27 of the first embodiment, will be associated with the apparatus 64 to automatically determine the relative humidity once the dew point temperature is sensed through an imbalance or sudden change in the signal from a particular pair of the opposed heat sensors in the heat sinks 66 and 68.

From the foregoing it will be seen that the present dew point measuring apparatus is uniquely adapted to immediately sense the point of condensation of a gas by detecting an abrupt change in the rate of heat flow, and measuring the temperature of the condensation surface at that point The concept is applicable not only to the specific industrial drying process described but is equally useful in determining and accurately measuring relative humidity in a variety of other applications.

Various modifications and changes may be made with regard to the foregoing detailed description without departing from the spirit of the invention.

We claim:

1. Dew point temperature measuring apparatus comprising:
   heat flow sensor means having a condensing surface means and operative upon a flow of heat through said condensing surface means to generate an output signal proportional to the rate at which said heat flows through said condensing surface means;
   temperature change means to bring the temperature of said condensing surface means to the dew point temperature of a gas flowing adjacent said condensing surface means;
   temperature sensor means to measure the surface temperature of said condensing surface means; and
   detecting means for determining a significant change in said output signal from said heat flow sensor means thereby to determine the occurrence of condensation on said condensing surface means whereby, the temperature measured by said temperature sensor means, when said detecting means detects said significant change in said output signal, is indicative of the dew point temperature.

2. Dew point temperature measuring apparatus according to claim 1 wherein said heat flow sensor means comprises a thermopile.

3. Dew point temperature measuring apparatus according to claim 1 wherein said heat flow sensor means comprises a pair of matched heat flow sensors and wherein said condensing surface means comprises a pair of condensing surfaces for said heat flow sensors, respectively, arranged in the flow path of said gas; wherein said temperature change means includes cooling means operative to maintain one of said heat flow sensors at a temperature slightly cooler than the other of said heat flow sensors; wherein said detecting means includes means connecting the output signals of said heat flow sensors to obtain the algebraic difference whereby a significant change in the resulting composite output signal occurring upon said condensation is more readily detectable; and wherein said temperature sensor means is associated with the cooler one of said heat flow sensors.

4. Dew point temperature measuring apparatus according to claim 1 wherein said temperature change means comprises a heat sink in thermal association with said heat flow sensor means, and further comprises cooling means for cooling said condensing surface of said heat flow sensor means.

5. Dew point temperature measuring apparatus according to claim 3 wherein said temperature change means further includes heating means actuable for heating the condensing surfaces of said pair of heat flow sensors; and wherein said detecting means is responsive to a change in said composite output signal resulting from said condensation to actuate said heating means for raising the temperature of said condensing surfaces above said dew point temperature, said detecting means further being responsive to a change in said composite output signal resulting from a cessation in and evaporation of said condensation to deactivate said heating means and enable said cooling means to lower the temperature of said condensing surfaces toward said dew point temperature.

6. Dew point temperature measuring apparatus according to claim 1 wherein said heat flow sensor means comprises pairs of matched first and second heat flow sensors having their condensing surfaces arranged in opposed relation; said pairs being arranged in spaced relation along the flow path of said gas; wherein said temperature sensor means comprises:
    temperature sensors associated with the condensing surfaces of said first heat flow sensors, respectively; wherein said temperature change means is operative to maintain the condensing surfaces of said pairs at different temperatures along said flow path, and is further operative to maintain each of said first heat flow sensors at a temperature slightly cooler than its associated second heat flow sensor; and wherein said detecting means includes means connecting the output signals of said first and second heat flow sensors of each of said pairs to obtain the algebraic difference whereby a significant change in the resulting composite output signal occurring upon condensation upon the condensing surface of said first heat flow sensor of a particular one of said pairs indicates that the temperature of said condensation surface of said first heat flow sensor of said particular one of said pairs is the dew point temperature of said gas.

7. Dew point temperature measuring apparatus according to claim 6 wherein said temperature change means comprises first and second wedge shape heat sinks spaced apart to define said flow path, with said first and second heat sinks increasing in mass in a downstream direction; wherein said temperature change means includes cooling means in thermal association with said first heat sink; and wherein said first and second heat flow sensors are in thermal association with said first and second heat sinks, respectively.

8. Dew point temperature measuring apparatus comprising:
    first and second adjacent matched heat flow sensors having first and second condensing surfaces, respectively, arranged in a flow path of a gas and operative upon a flow of heat through said condensing surfaces to generate output signals proportional to the rate at which said heat flows through said condensing surfaces, respectively;
    temperature change means to bring the temperature of the condensing surfaces of said first and second heat flow sensors toward the dew point temperature of said gas, and including cooling means operative to maintain said first condensing surface at a temperature slightly lower than said second condensing surface whereby condensation at said dew point temperature will first occur upon said first condensing surface;
    temperature sensor means to measure the surface temperature of said first condensing surface; and
    detecting means connecting the output signals of said first and second heat flow sensors in series opposition whereby said output signals are algebraically summed to provide a composite control signal which changes abruptly upon occurrence of said condensation whereby, the temperature measured by said temperature sensor means, when said detecting means detects an abrupt change in said composite control signal, is indicative of the dew point temperature.

9. Dew point temperature measuring apparatus according to claim 8 wherein said first and second heat flow sensors are thermopiles.

10. Dew point temperature measuring apparatus according to claim 8 wherein said cooling means comprises heat sink means in thermal association with said first and second heat flow sensors for cooling said first and second condensing surfaces toward said dew point temperature, and thermal barrier means disposed in the heat flow path between said second condensing surface and said heat sink means for maintaining said first condensing surface at said temperature slightly cooler than said second condensing surface, said first and second condensing surfaces being otherwise essentially isothermal.

11. Dew point temperature measuring apparatus according to claim 8 and including means defining said flow path and operative to pass a sample of said gas along said flow path and across said first and second condensing surfaces in a substantially steady state condition.

12. Dew point temperature measuring apparatus according to claim 8 wherein said temperature change means further includes heating means actuable for heating said first and second condensing surfaces; and
    wherein said detecting means is responsive to a change in said composite control signal resulting from said condensation to actuate said heating means for raising the temperature of said condensing surfaces above said dew point temperature, said detecting means further being responsive to a change in said composite control signal resulting from a cessation in and evaporation of said condensation to deactuate said heating means and enable said cooling means to lower the temperature of said condensing surfaces toward said dew point temperature.

13. Dew point temperature measuring apparatus according to claim 8 including heating means actuable for heating said first and second condensing surfaces, and wherein said detecting means comprises:
- first logic means operative to produce said composite control signal in response to a detected difference between the output signals of said first and second heat flow sensors;
- second logic means operative to compute a desired dew point temperature in response to a temperature signal and a pressure signal, and to a predetermined relative humidity of the gas which is to be maintained;
- third logic means, responsive to said first and second logic means, for actuating means for introducing dry gas into said gas when said temperature of said first condensing surface is at least as high as said desired dew point temperature at the time said first logic means produces said composite control signal; and
- means responsive to said first logic means to actuate said heating means at the time said first logic means products said composite control signal.

14. Dew point temperature measuring apparatus according to claim 13 wherein said first logic means is operative to detect both electrically positive and electrically negative differences between the output signals of said first and second heat flow sensors, and said means is responsive to said first logic means to actuate also deactuates said heating means, respectively, depending upon whether said composite control signal represents an electrically positive or electrically negative difference, whereby said first and second condensing surfaces are heated and cooled cyclically above and below said dew point temperature.

* * * * *

UNITED STATES PATENT AND TRADEMARK OFFICE
CERTIFICATE OF CORRECTION

PATENT NO. : 4,579,462
DATED : April 1, 1986
INVENTOR(S) : Dieter Rall and David R. Hornbaker It is certified that error appears in the above-identified patent and that said Letters Patent is hereby corrected as shown below:

Column 2, line 53, delete 2,904,95" and insert "2,904,995;

Column 14, line 5, delete "products" and insert "produces; and

Column 14, line 11, delete "is".

Signed and Sealed this

Eighth Day of July 1986

[SEAL]

Attest:

DONALD J. QUIGG

Attesting Officer

Commissioner of Patents and Trademarks